United States Patent [19]

Iinuma

[11] Patent Number: 5,448,994
[45] Date of Patent: Sep. 12, 1995

[54] APPARATUS FOR PERFORMING MEDICAL TREATMENT BY USING ELECTROACOUSTIC TRANSDUCER ELEMENT

[75] Inventor: Kazuhiro Iinuma, Tochigi, Japan

[73] Assignee: Kabushiki Kaisha Toshiba, Tokyo, Japan

[21] Appl. No.: 254,665

[22] Filed: Jun. 6, 1994

Related U.S. Application Data

[63] Continuation of Ser. No. 941,861, Sep. 8, 1992, abandoned, which is a continuation of Ser. No. 662,207, Feb. 28, 1991, abandoned.

[30] Foreign Application Priority Data

Feb. 28, 1990 [JP] Japan .................. 2-45496

[51] Int. Cl.⁶ ............................................. A61B 17/22
[52] U.S. Cl. ................... 128/660.03; 601/3; 601/4; 607/97
[58] Field of Search ............. 128/660.03; 601/2-4; 607/97

[56] References Cited

U.S. PATENT DOCUMENTS

| | | | |
|---|---|---|---|
| 4,803,995 | 2/1989 | Ishida et al. ............................. | 601/4 |
| 4,955,366 | 9/1990 | Uchiyama et al. ............ | 128/24 EL |
| 4,962,754 | 10/1990 | Okazaki ..................... | 128/660.03 |
| 5,048,527 | 9/1991 | Okazaki ..................... | 128/660.03 |
| 5,062,412 | 11/1991 | Okazaki ..................... | 128/24 EL |

*Primary Examiner*—Ruth S. Smith
*Attorney, Agent, or Firm*—Foley & Lardner

[57] ABSTRACT

An acoustic medical treatment apparatus using electroacoustic transducer elements. The apparatus includes a concave transducer for causing divided partial transducers to generate strong ultrasonic waves on a living body and detecting ultrasonic waves reflected by the living body, pulsers arranged in correspondence with the partial transducers for driving them, a controller for controlling the pulsers to cause the concave transducer to emit the strong ultrasonic waves or weak ultrasonic waves, a reception system for receiving reflected ultrasonic waves, which propagate in ultrasonic wave propagation paths between the partial transducers and an object to be irradiated in the living body, through the respective partial transducers, when weak ultrasonic waves are emitted from the concave transducer under the control of the controller, and processes the respective reception signals, and a monitor for displaying information of the ultrasonic propagation paths by using each processed signal obtained by the reception system.

33 Claims, 10 Drawing Sheets

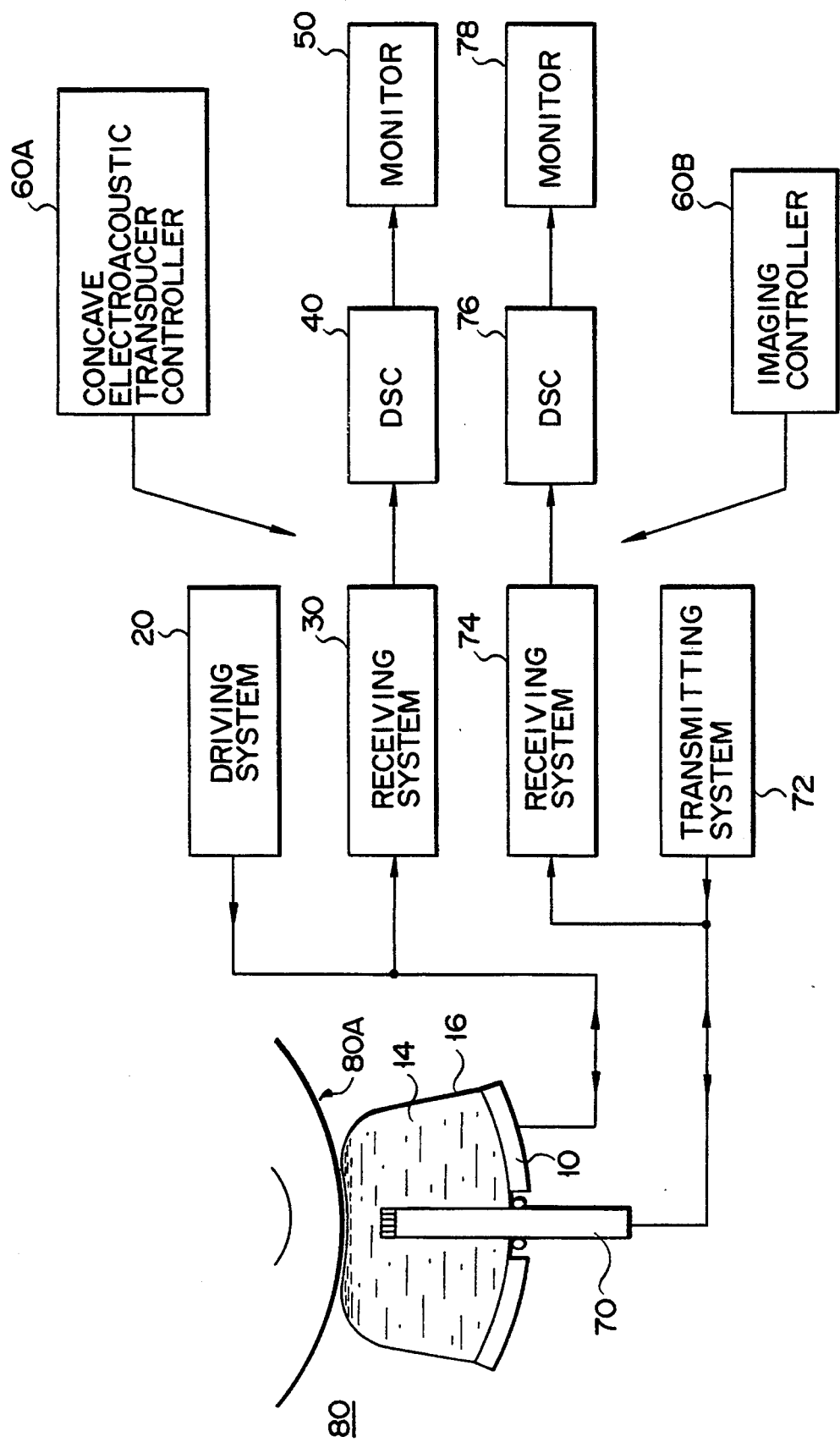
F I G. 4

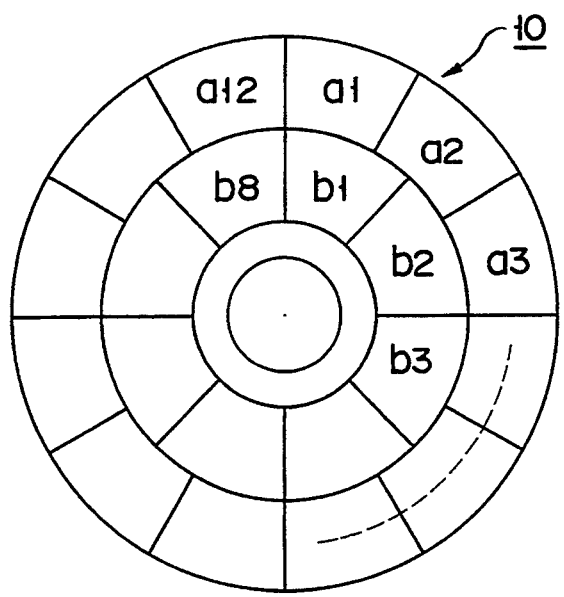
F I G. 7
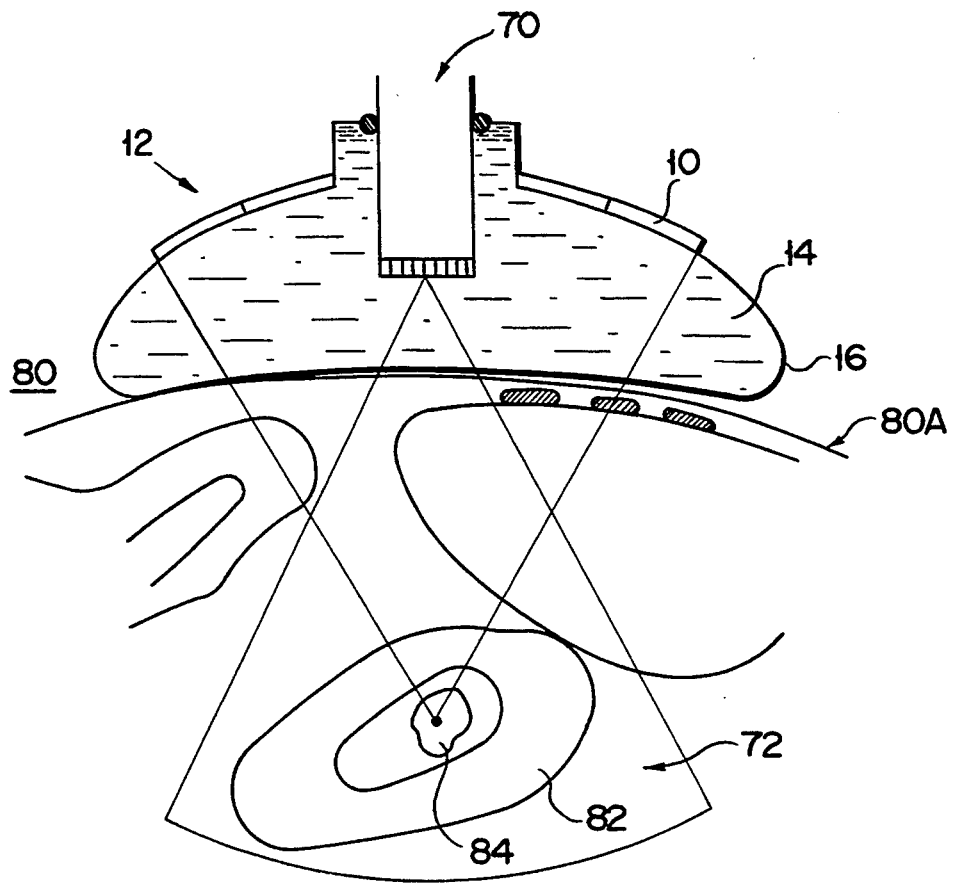
F I G. 8

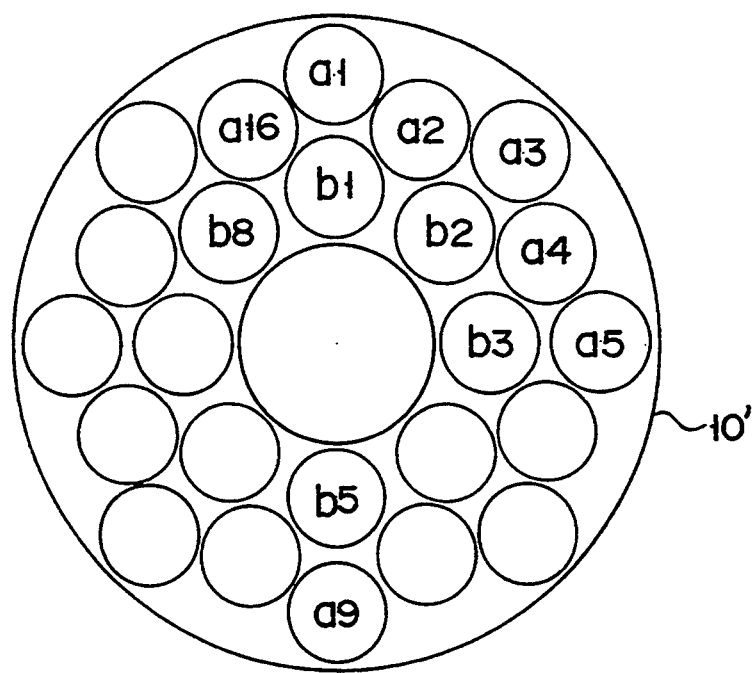
F I G. 12

APPARATUS FOR PERFORMING MEDICAL TREATMENT BY USING ELECTROACOUSTIC TRANSDUCER ELEMENT

This application is a continuation of application Ser. No. 07/941,861, filed Sep. 8, 1992, now abandoned, which is a continuation of application Ser. No. 07/662,207, filed Feb. 28, 1991, now abandoned.

BACKGROUND OF THE INVENTION

1. Field of the Invention

The present invention relates to an apparatus for medical treatment by using the energy of a sound wave, such as an ultrasonic wave generated by a piezoelectric element or an electroacoustic transducer element using electromagnetic induction and, more particularly, to an acoustic medical treatment apparatus such as a stone disintegration apparatus for generating a shock wave (to be referred to as a strong ultrasonic wave) by using, e.g., an electroacoustic transducer element, and disintegrating a stone (calculus) in a body by radiating strong ultrasonic wave on the stone, or a medical treatment apparatus (hyperthermia apparatus) for radiating a continuous ultrasonic wave from an electroacoustic transducer element onto cancer cells in a body so as to perform thermotherapy of the cancer cells.

2. Description of the Related Art

A conventional acoustic medical treatment apparatus, e.g., a stone disintegration apparatus, is designed to radiate a strong ultrasonic wave from the outside of a body onto a stone, in a body, such as a renal calculus or a gallstone, to disintegrate it. In this stone disintegration apparatus, a concave transducer having a diameter of 30 to 40 cm is arranged in an applicator, and a strong ultrasonic wave is emitted from the transducer to a focal point. In this case, the applicator is positioned in relation to the body so as to match the focal position with the stone, and the stone is disintegrated by the energy of the strong ultrasonic wave. This concave transducer is a piezoelectric transducer as an electroacoustic transducer element and radiates an ultrasonic narrow pulse wave from its concave surface. In addition, a tomographic imaging ultrasonic probe can be inserted in a hole formed in the center of the concave transducer. Electronic sector scanning of each transducer of this ultrasonic probe is performed to display a tomographic image on a monitor. The position of the stone can be fixed to a desired position by observing the tomographic image. In this case, a strong ultrasonic wave propagates in the form of a cone. That is, the wave has a relatively large sectional plane near a body surface, and is gradually focused on one point toward the stone.

Owing to sector scanning, the image obtained by the ultrasonic probe has a sectorial shape. That is, the image is substantially observed as a point near the body surface and gradually spreads toward a given position in the body. For this reason, regions near the surface of the body of a patient, other than the above-mentioned point, become blind regions. Therefore, even if the lungs or an intestinal tract or a bone is present in the radiation path of a strong ultrasonic wave near the body surface, it is not displayed on a tomographic image. In addition, since the tomographic image represents a sectional plane, regions other than this sectional plane are not displayed and constitute a large blind region. In order to display a stone as clearly as possible, the ultrasonic probe is preferably located as close to the stone as possible. With such an operation, however, the blind region is increased accordingly. For this reason, image display cannot be performed throughout the propagation path of a strong ultrasonic wave.

Furthermore, a stone is normally located at a position several centimeters away from a body surface. If a bone, an intestinal gas, a portion of a lung, or the like is present in the propagation path of a strong ultrasonic wave, effective ultrasonic energy cannot be radiated on the stone. Moreover, a bone may be damaged, or an ultrasonic wave is reflected by a gas, so that the reflected wave scatters around. This may cause the living body to suffer from a pain or may inflict injury on the body.

SUMMARY OF THE INVENTION

It is, therefore, an object of the present invention is to provide an acoustic medical treatment apparatus which uses an electroacoustic transducer element and can select a proper radiation path of a sound wave used for medical treatment.

It is another object of the present invention is to provide an acoustic medical treatment apparatus which uses an electroacoustic transducer element and can efficiently perform medical treatment without danger by easily determining the presence/absence of a bone, a gas, or the like by observing the state of a blind region, which cannot be observed on an image obtained by an imaging ultrasonic probe.

In order to achieve the above objects, there is provided an acoustic medical treatment apparatus using an electroacoustic transducer element, comprising:

sound wave generating means, having a plurality electroacoustic transducer elements arranged to form a concave surface for forming a focal point, for causing the respective elements to generate sound waves upon the application of voltages to the elements;

driving control means for driving/controlling the plurality of electroacoustic transducer elements to selectively generate sound waves for medical treatment and sound waves for non-treatment;

reception means for receiving reflected sound waves in correspondence with the plurality of electroacoustic transducer elements when the sound wave generating means is driven by the driving control means to generate sound waves for non-treatment; and generating/display means for generating information associated with sound wave propagation paths between the plurality of electroacoustic transducer elements and the focal point on the basis of the reflected sound wave signals received by the reception means and for displaying the generated information.

In addition, in order to achieve the above objects, according to the present invention, there is provided an acoustic medical treatment apparatus using an electroacoustic transducer element, comprising:

sound wave generating means, having a plurality electroacoustic transducer elements arranged to form a concave surface for forming a focal point, for causing the respective elements to generate sound waves upon application of voltages to the elements;

driving control means for driving/controlling the plurality of electroacoustic transducer elements to selectively generate sound waves for medical treatment and sound waves for non-treatment;

reception means for receiving reflected sound waves in correspondence with the plurality of electroacoustic transducer elements when the sound wave generating means is driven by the driving control means to generate sound waves for non-treatment;

generating/display (or detecting) means for generating information associated with sound wave propagation paths between the plurality of electroacoustic transducer elements and the focal point on the basis of the reflected sound wave signals received by the reception means and for displaying the generated information;

an imaging ultrasonic probe inserted in a substantially central portion of a concave surface of the sound wave generating means, arranged along a direction to the focal point, and constituted by a large number of small ultrasonic transducers; and tomographic image imaging means for scanning/driving each of the ultrasonic vibrators of the ultrasonic probe to generate a tomographic image, and displaying the tomographic image.

Furthermore, in order to achieve the above objects, according to the present invention, there is provided an acoustic medical treatment apparatus using an electroacoustic transducer element, comprising:

an applicator having a bag in which an ultrasonic propagation medium is stored, the bag being brought into contact with a surface of a living body;

ultrasonic wave generating means, arranged in the applicator and having a plurality of electroacoustic transducer elements arranged to form a concave surface for forming a focal point, for causing the respective elements to generate sound waves upon the application of voltages to the elements;

driving control means for driving/controlling the plurality of electroacoustic transducer elements to selectively generate high-energy ultrasonic waves for medical treatment and ultrasonic waves for non-treatment;

reception means for receiving reflected ultrasonic waves in correspondence with the plurality of electroacoustic transducer elements when the ultrasonic wave generating means is driven by the driving control means to generate ultrasonic waves for non-treatment;

generating/display means for generating information associated with ultrasonic wave propagation paths between the plurality of electroacoustic transducer elements and the focal point on the basis of the reflected ultrasonic wave signals received by the reception means and for displaying the generated information;

an imaging ultrasonic probe inserted in a substantially central portion of a concave surface of the sound wave generating means, arranged along a direction to the focal point, and constituted by a large number of small ultrasonic transducers; and tomographic image imaging means for scanning/driving each of the ultrasonic transducers of the ultrasonic probe to generate a sector tomographic image, and displaying the sector tomographic image.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a block diagram showing an overall arrangement of an acoustic medical treatment apparatus, such as a stone disintegration apparatus or a hyperthermia apparatus, according to the first embodiment, which is designed to radiate a sound wave on a lower portion of a living body, and specifically showing a system for independently controlling a section for medical treatment and a section for ultrasonic imaging;

FIG. 7 is a schematic plan view showing a concave transducer divided into a plurality of partial transducers mounted in an applicator of the stone disintegration apparatus;

FIG. 8 is a schematic sectional view showing a positional relationship between a living body and an applicator in which a concave transducer, an ultrasonic probe, and the like are mounted;

FIG. 12 is a schematic plan view showing another embodiment of an arrangement of concave transducers.

DETAILED DESCRIPTION OF THE PREFERRED EMBODIMENTS

Figure 1:
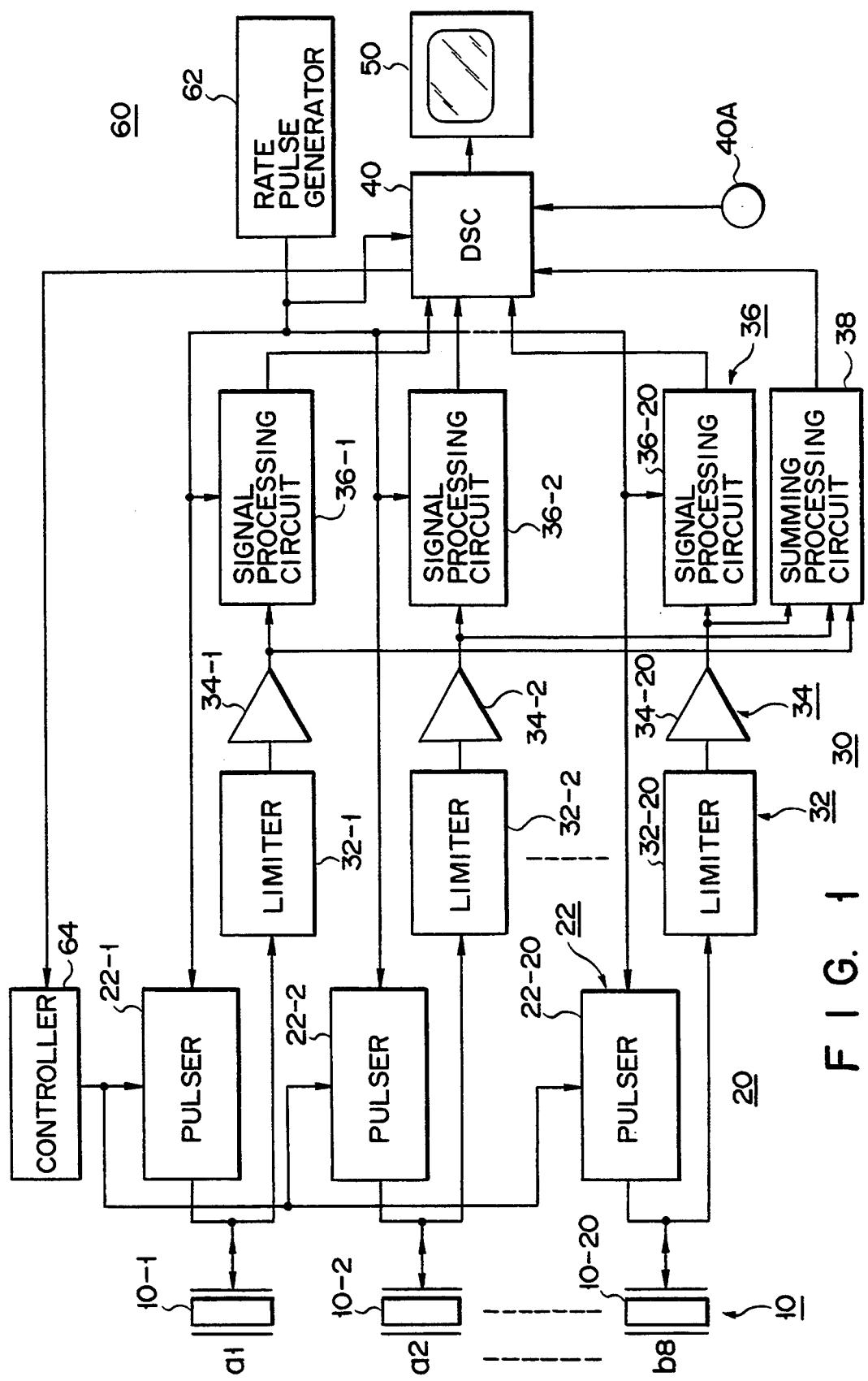
FIG. 1 is a block diagram showing only components, of a stone disintegration apparatus, associated with medical treatment, as an embodiment of an acoustic medical treatment using an electroacoustic transducer element according to the present invention.

FIG. 1 is a block diagram showing only components, of a stone disintegration apparatus, associated with stone disintegration, as an embodiment of an acoustic medical treatment apparatus according to the present invention. A stone disintegration apparatus having a general medical treatment (stone disintegration) function and an imaging function is realized by applying the arrangement shown in FIG. 1 to any one of acoustic medical treatment apparatuses shown in FIGS. 3 to 6.

Figure 2:
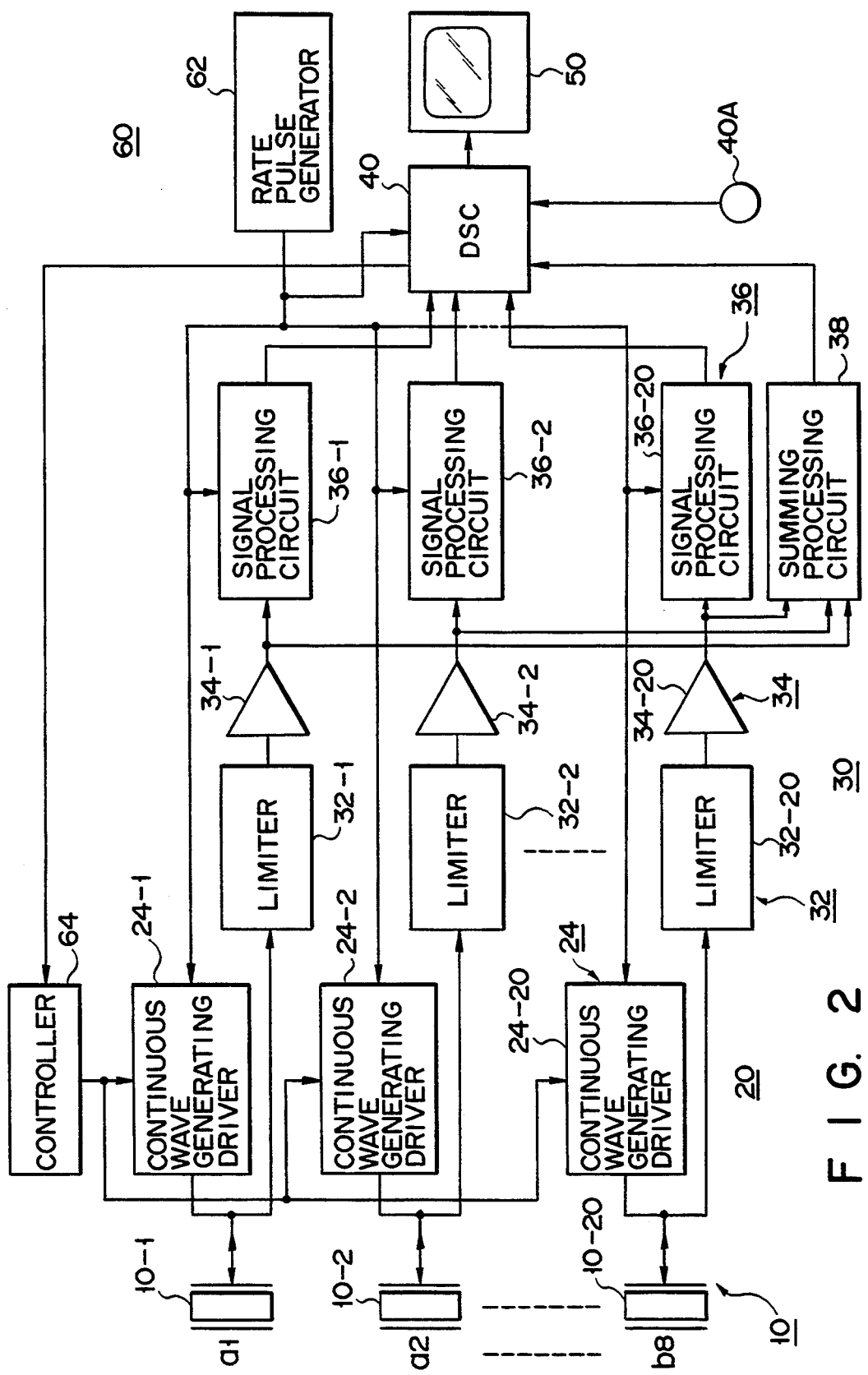
FIG. 2 is a block diagram showing a main part of a hyperthermia apparatus as an embodiment of the acoustic medical treatment apparatus using an electroacoustic transducer element according to the present invention.

FIG. 2 is a block diagram showing only components, of a hyperthermia apparatus, associated with hyperthermia treatment, as an embodiment of the acoustic medical treatment apparatus according to the present invention. A hyperthermia apparatus having a general medical treatment (hyperthermia treatment) function and an imaging function is realized by applying the arrangement shown in FIG. 2 to any one of the acoustic medical treatment apparatuses.

FIGS. 7 and 12 show concave transducers in these stone disintegration apparatus and hyperthermia apparatus. FIG. 8 shows a positional relationship between a living body and an applicator in the stone disintegration apparatus or the hyperthermia apparatus. In addition, FIGS. 9 to 11 respectively show display forms for displaying the intensities of reception signals in the stone disintegration apparatus or the hyperthermia apparatus.

An arrangement of a stone disintegration apparatus of this embodiment, which is specified by FIGS. 1, 3, 7, and 8, will be described-below. The components for stone disintegration shown in FIG. 1 includes a concave transducer 10 as an electroacoustic transducer element, a driving system 20 including pulsers 22 (22-1–22-20), a receiving system 30 including limiters 32 (32-1–32-20), preamplifiers 34 (34-1 to 34-20), signal processing circuits 36 (36-1 to 36-20), and a summing processing circuit 38, a DSC 40 including a freeze button 40A, a monitor 50, and a control system 60 (60A) including a rate pulse generator 62 and a controller 64.

Figure 3:
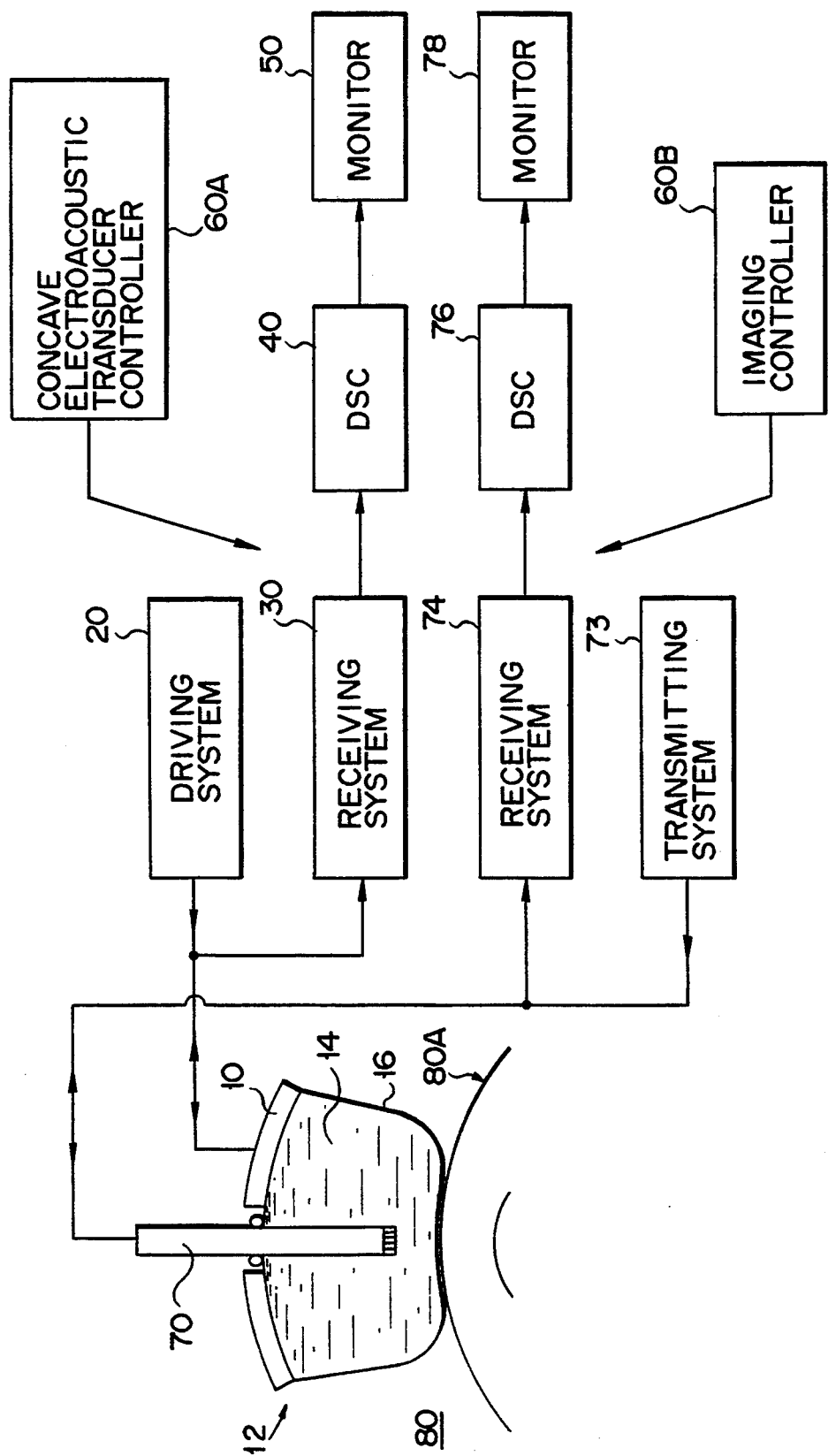
FIG. 3 is a block diagram showing an overall arrangement of an acoustic medical treatment apparatus, such as a stone integration apparatus or a hyperthermia apparatus, according to the first embodiment of the present invention, which is designed to radiate a sound wave on an upper portion of a living body, and specifically showing a system for independently controlling a section for medical treatment and a section for ultrasonic imaging.

A stone disintegration apparatus shown in FIG. 3 comprises the components for stone disintegration, which includes the concave transducer 10, the driving system 20, the receiving system 30, the DSC 40, the monitor 50, and the control system 60 (60A) shown in FIG. 1, and a tomographic imaging system for imaging a sector tomographic image (B mode image), which includes an image ultrasonic probe 70, a transmitting system 72, a receiving system 74, DSC 76, a monitor 78, and an imaging controller 60B.

Each component for stone disintegration will be described below. The concave transducer 10 is constituted by, e.g., a piezoelectric element having a concave surface and is arranged in an applicator 12 shown in FIGS. 3 or 8. The concave transducer 10 is driven by the pulser 22 to emit a strong ultrasonic pulse (shock wave) or a weak ultrasonic pulse.

As shown in FIG. 7, the concave transducer 10 consists of two annular members in contact with each other. These annular members are divided into a plurality of different partial transducers. For example, the outside annular member of the concave transducer 10 is divided into 12 equal portions (a1, a2, a12), while the inside annular member is divided into 8 equal portions (b1, b2, ... b8). That is, the concave transducer 10 is divided into 20 portions as a whole. These partial transducers (a1–a12, b1–b8) are electrically connected to the pulsers 22 constituting the driving system 20 and to the limiters 32, each serving as an element of the reception system 30.

As shown in FIGS. 3 and 8, the applicator 12 is equipped with the concave transducer 10, a medium, e.g., water 14, a rubber film 16 for containing each of the water 14, the ultrasonic probe 70, a mechanism (not shown) for operating the ultrasonic probe 70.

A strong ultrasonic pulse emitted from the concave transducer 10 propagates to a kidney 82 through the water 14, the rubber film 16, and a body surface 80A of a living body 80. As shown in FIG. 8, the ultrasonic wave propagates in the form of a cone. That is, the sectional plane of the wave is wide near the concave transducer 10 and gradually narrows toward a stone 84. This is because the transducer 10 has a concave sound wave emission surface and is constituted by an annular member.

The ultrasonic probe 70 is inserted in a hole in the center of the concave transducer 10 and is sector-scanned by the transmitting system 73 to monitor the position of the stone 84 existing in the kidney 82. When sector scanning of the ultrasonic probe 70 is performed, a tomographic image of a sectorial plane or slice 72 around the stone 84 in the kidney 82 can be obtained on the monitor 78. The sectional plane 72 of sector scanning by the ultrasonic probe 70 gradually broadens downward to constitute a sectorial plane.

Referring to FIG. 1, the rate pulse generator 62 generates a rate pulse of several Hz and supplies it to each pulser 22. The pulsers 22 constituting the driving system 20 drive the respective partial transducers (a1–b8) arranged on the concave transducer 10 in response to the rate pulse supplied from the rate pulse generator 62. The partial transducers (a1–b8) are respectively driven by the pulsers 22 to emit ultrasonic pulses. The ultrasonic pulses propagate in the living body 80.

The controller 64 supplies signals for controlling outputs from the pulsers 22. For example, the controller 64 controls the following modes: a large output pulse mode for generating a strong ultrasonic pulse; an intermediate output pulse mode for causing only some of the partial transducers to generate strong ultrasonic pulses; a small output pulse mode for generating weak ultrasonic pulses for monitoring; a selective driving mode for selectively driving the partial transducers; and a stop mode for stopping a pulse output operation.

The respective partial transducers a1 to b8 detect ultrasonic waves reflected by the living body 80 and output electrical signals to the preamplifier 34 through the limiters 32. Each limiter 32 performs a limiting operation with respect to the echo signal input from a corresponding partial transducer so as to obtain only a desired signal component. Each preamplifier 34 amplifies the desired echo signal component input from a corresponding limiter 32 to a predetermined level. Each signal processing circuit 36 detects the amplified signal input from a corresponding preamplifier 34 by using an envelope detector, performs level adjustment of an obtained signal for a tomographic image, further performs signal processing such as A/D conversion (analog/digital conversion), and supplies the processed signal to the DSC (digital scan converter) 40. The DSC 40 has a frame memory and writes the processed signal, input from each signal processing circuit 36, in the frame memory. More specifically, the DSC 40 writes the respective processed signals in the frame memory by using address signals (not shown) in correspondence with the respective partial transducers, thus forming image patterns shown in FIGS. 9 to 11. In addition, the DSC 40 converts the scan format of each processed signal written in the frame memory from the ultrasonic scan format to, e.g., the standard TV scan format, and, at the same time, supplies the image pattern shown in FIG. 9 to the monitor 50.

An operation of this embodiment having the above-described arrangement will be described below. The controller 64 is set in the stop mode, and a bag 16 of the applicator 12 is brought into contact with the body surface 80A of the living body 80. Subsequently, sector scanning is performed by the ultrasonic probe 70 to display a tomographic image on the monitor 78 shown in FIG. 3. Furthermore, the applicator 12 is moved to superpose an image of the stone 84 on the tomographic image. The position and angle of the applicator 12 are then set to position the focal point of the concave transducer 10 on the stone 84.

The controller 64 is set in the small output pulse mode so that the partial transducers a1 to b8 are respectively driven by the pulsers 22 to emit weak ultrasonic pulses. Ultrasonic waves reflected by the living body 80 and received by the partial transducers a1 to b8 are added/processed by the addition processing circuit 38. The obtained signal is output to the monitor 50 through the DSC 40. As a result, reflection caused by the stone 84 can be detected through the monitor 50.

In this case, since the distance from the concave transducer 10 to the focal position is constant, pulses which fall within a certain range of time required for a pulse emitted from the concave transducer 10 to propagate to the focal position and return to the transducer 10 (about 133 $\mu$s per 10 cm) are detected. When the stone 84 and the focal point coincide with each other, a strong reflected pulse is detected.

At the same time, reflected wave signals received by the partial transducers a1 to b8 reflectively pass through the pulsers 22, limiters 32, the preamplifiers 34, and the signal processing circuits 36 and are input to the DSC 40. These signals are then displayed on the monitor 50 by various display schemes.

A first display pattern displayed on the monitor 50 will be described later. The intensities of waves reflected by the stone 84 are subjected to luminance modulation in the signal processing circuits 36. The modulated signals are then written in the DSC 40 in correspondence with the positions of the partial transducers a1 to b8. Reflected wave data is read out from the DSC 40 to be displayed on the monitor 50 in correspondence with the levels of luminance (brightness).

Figure 9:
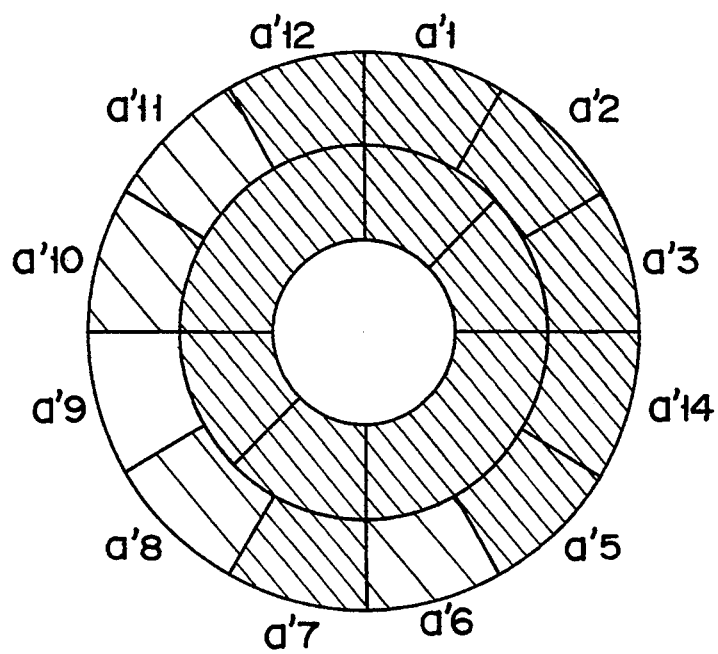
FIG. 9 is a view showing a first display form for displaying the intensities of reception signals in a section for medical treatment.

If no obstacles, e.g., a gas and bones, are present in propagation paths between the stone 84 and given partial transducers, strong reflected waves such as waves a1', ..., a5', a7', and a12' are received in accordance with the given partial transducers, as shown in FIG. 9. As a result, the luminances of portions, of the display pattern displayed on the monitor 50, corresponding to the given transducers, are increased.

If obstacles are present in the propagation paths of ultrasonic waves, weak reflected wave outputs (example, reference to FIG. 9) such as wave outputs A'6, A'8, A'10, and A'11 and A'11 or A'9 are detected in accordance with the sizes and qualities of the obstacles. As a result, the luminances of the portions of the display pattern on the monitor 50, corresponding to the transducers which receive the weak reflected waves, are decreased.

Since the luminance of a signal is changed depending on the intensity of reflection, the state of an obstacle in a propagation path can be easily obtained by checking this luminance. Instead of the luminance display scheme, a flicker display scheme may be employed, in which the frequency of flicker is increased with a decrease in reflection intensity.

In this case, each partial transducer is required to have an area (opening) large enough to ensure a sufficient focusing effect so that ultrasonic waves from the respective partial transducers propagate in their own paths without much overlapping.

Figure 10:
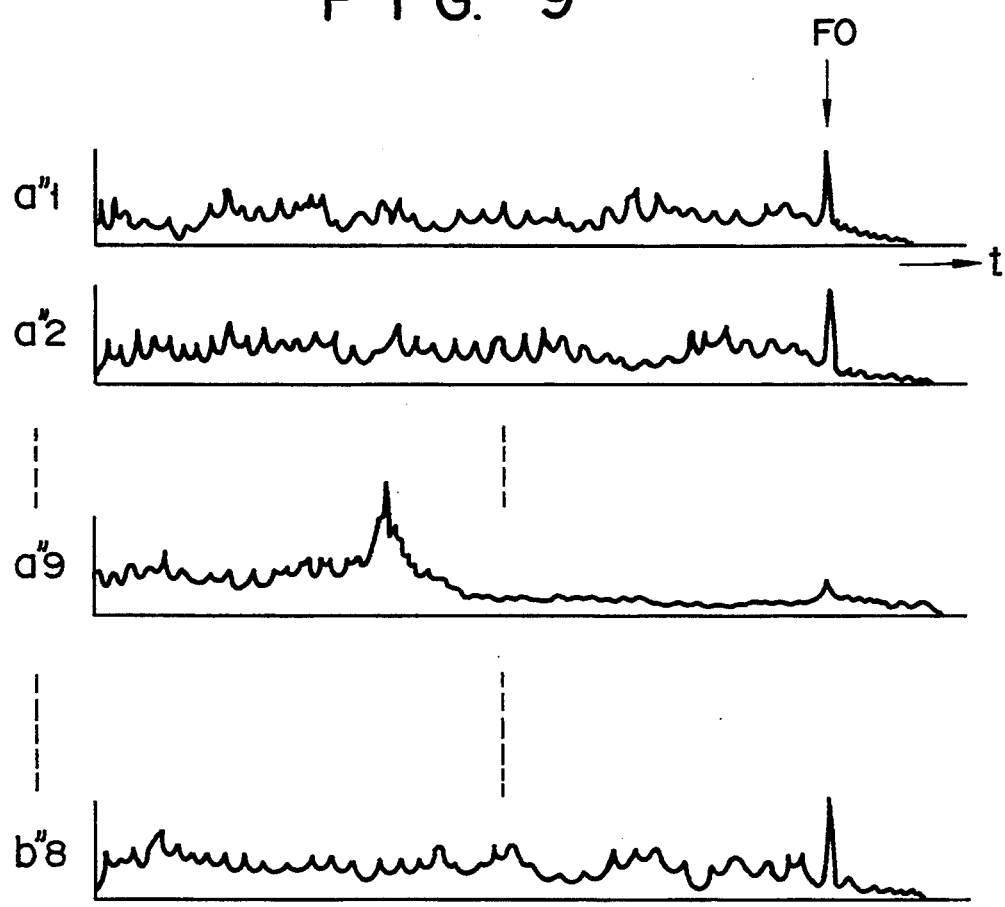
FIG. 10 is a view showing a second display form for displaying the intensities of reception signals in the section for medical treatment.

A second display pattern of the intensities of waves reflected by the stone 84 will be described below with reference to FIG. 10. Referring to FIG. 10, the amplitudes of signals received by the partial transducers a1 to b8 are properly processed by the signal processing circuits 36, and the obtained outputs are plotted along the ordinate axis of the monitor 50. In addition, time t after the emission of a pulse, i.e., a distance from a partial transducer, is set on the axis of abscissa of the monitor 50. With this setting, the intensity of a reflected wave received by each partial transducer is displayed. In the case shown in FIG. 10, since signals $a''_1$, $a''_2$, and $b''_8$ received by the partial transducers $a_1$, $a_2$, and $b_8$ exhibit strong reflected waves in the paths from the partial transducers to the stone (focal point $F_0$), it can be determined that special large obstacles exist. However, since a strong reflecting object, e.g., an intestinal gas, is present midway along the propagation path between the transducer and the stone, strong reflection occurs at the object. As a result, it is detected that the energy of an ultrasonic wave reaching the stone is reduced, and reflection by the stone is weakened.

A third display pattern of the intensities of reflected waves will be described below with reference to FIG. 11. The third display pattern includes a pattern of the concave transducer, which is viewed from its upper surface, and a perspective pattern obtained by viewing the propagation paths of ultrasonic waves between the concave transducer and the stone or the focal point $F_0$ when viewed from the side of the perspective pattern. Alternatively, the third display pattern may be constituted by only the pattern obtained by viewing the propagation paths, of ultrasonic waves, between the concave transducer and the stone or the focal point $F_0$.

Figure 11:
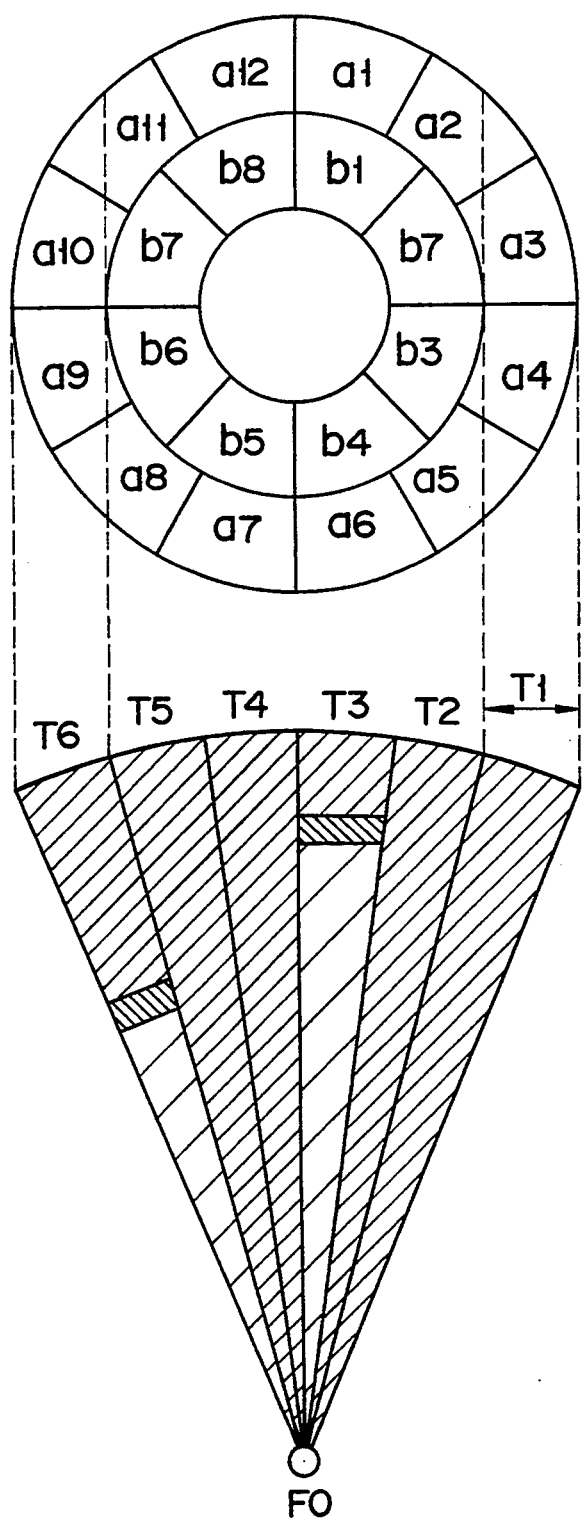
FIG. 11 is a view showing a third display form for displaying the intensities of reception signals in the section for medical treatment.

Referring to FIG. 11, the propagation paths of ultrasonic waves are divided into regions ($T_1$ - $F_0$), ($T_2$ - $F_0$), ... ($T_6$ - $F_0$). The intensities of ultrasonic waves shown in FIG. 9 are luminance-modulated in units of the divided paths and are displayed on the monitor 50. In this case, a substantially perspective image is displayed. For example, therefore, an addition average signal based on the area ratios of signals received by the partial transducers $a_2$, $a_3$, $a_4$, and $a_5$, which fall within a region $T_1$, is used for the regions ($T_1$ - $F_0$). In this case, since the area ratios are:

$a_2:a_3:a_4:a_5 = 0.3:0.9:0.9:0.3$ an addition average signal is given by:

$(a''_2 \times 0.3 + a''_3 \times 0.9 + a''_4 \times 0.9 + a''_5 \times 0.3) \div 2.4$ For the regions $T_2$, ... $T_6$, addition average signals are obtained in the same manner as for the region $T_1$.

The regions $T_1$, ... $T_6$ may be divided into smaller regions. In this embodiment, since a large obstacle exists midway along the path on the left end in relation to an observer (the path of the partial transducer $a_9$), strong reflection is indicated at the corresponding portion, and the reflection is weakened in the subsequent portion of the path, i.e., from the obstacle to the focal point $F_0$.

As is apparent from strong reflection in the region $T_3$, an obstacle is present in the path of the partial transducer $a_6$. By simultaneously observing the display pattern in FIG. 9 and the display pattern obtained by viewing the concave transducer from its upper surface in FIG. 11, an operator can easily detect a three-dimensional positional relationship between an obstacle and the concave transducer.

If the perspective display pattern in FIG. 11, which is obtained by viewing the propagation paths, is displayed while superposing it on a tomographic image obtained by the ultrasonic probe, a relationship between an organ and the path of a radiated ultrasonic wave can be easily detected. These superposed images can be intermittently frozen by the freeze button 40A shown in FIG. 1 so as to prevent wasteful emission of ultrasonic waves.

By monitoring this state, the applicator 12 can be set at an optimal position, in relation to the living body, at which only a few obstacles are present. In this case, the focal point is matched with the stone, and the display patterns in FIGS. 9 to 11 are displayed. An optimal applicator position where the focal point always coincides with the stone can be easily set by rotating a support mechanism (not shown) of the applicator 12 about the focal position. After the optimal position is determined in this manner, the controller 64 is set in the large output pulse mode to emit strong ultrasonic waves.

If an obstacle in a propagation path cannot be avoided, the controller 64 is set in the partial large output pulse mode to stop emission of strong ultrasonic waves from partial transducers corresponding to the path in which the obstacle is present and to cause other partial transducers to emit strong ultrasonic waves. This operation may be manually performed. However, driving of the corresponding partial transducers can be automatically stopped on a condition that the intensities of waves reflected by the stone, which are shown in, e.g., FIGS. 9 or 10, are equal to or lower than a predetermined value.

In addition, a flickering indication resulting from active electroacoustic transistor elements and echo waves, as shown in FIGS. 9 and 11, are superimposed on each other and displayed. Therefore, an operator can clearly understand if the transducer is off-driving or on-driving.

In this method, therefore, radiation of unnecessary strong ultrasonic waves into a living body can be prevented. This increases the safety of a living body and relieves pain.

The shapes and number of partial transducers are not limited to those shown in FIG. 1. For example, circular partial transducers may be used, as shown in FIG. 12. In addition, each partial transducer may be constituted by a combination of a plurality of transducers. If one partial transducer is constituted by a combination of smaller transducers, the degree of freedom in combination is greatly increased to allow finer control.

The above-described embodiment is associated with the method of independently receiving reception signals in units of partial transducers. However, since the directivity of transmission is the same as that of reception, the same effect as described above can be obtained by independently transmitting signals from the respective partial transducers.

More specifically, the partial transducers $a_1$, $a_2$, ... are sequentially driven by the controller 64 in the small output pulse mode. A reflected wave may be received by a corresponding partial transducer at each driving operation, or may be received by all the transducer, and the received waves are used as signals respectively corresponding to the paths of the partial transducers.

In the above embodiment, stone disintegration is exemplified. However, the present invention is not limited to stone disintegration and can be equally applied to, e.g., an ultrasonic hyperthermia treatment and a treatment for cancer by strong ultrasonic waves. In this case, a strong ultrasonic wave may be a pulse wave or a continuous wave. This will be described later.

In the above embodiment, a piezoelectric transducer is exemplified as a means for generating a strong ultrasonic wave. However, an element based on electromagnetic induction may be used. Such an element is designed such that a metal plate is placed on a spiral coil. When a large current is instantaneously supplied to the coil, a shock wave is generated from a surface of the metal plate. Therefore, the same arrangement as that of the concave transducer shown in FIG. 1 can be realized by using a plurality of such elements as partial transducers. In this case, in order to increase the sensitivity of a reception signal, reception signals received by a plurality of electromagnetic induction partial transducers may be used. Alternatively, piezoelectric elements may be arranged between the partial transducers, and a combination thereof may be used.

Furthermore, in the above embodiment, the intensities of reflected waves are displayed in correspondence with luminance modulation. However, the intensities of reflected waves may be displayed by, e.g., a color display scheme.

The stone disintegration apparatus specified by FIGS. 1 and 3 has been described above. As shown in FIG. 3, this stone disintegration apparatus is designed to radiate a shock wave on an upper portion of a living body and, more specifically, a system for independently controlling a section for stone disintegration and a section for ultrasonic imaging. An applicator 12 is arranged in a living body 80. The system includes a convex electroacoustic transducer element controller 60A and an imaging controller 60B.

As shown in FIG. 4, a stone disintegration apparatus specified by FIGS. 1 and 4 is designed to radiate a shock wave on a lower portion of a living body and, more specifically, a system for independently controlling a section for stone disintegration and a section for ultrasonic imaging. An applicator 12 is arranged under a living body 80. The system includes a concave electroacoustic transducer element controller 60A and an imaging controller 60B.

Figure 5:
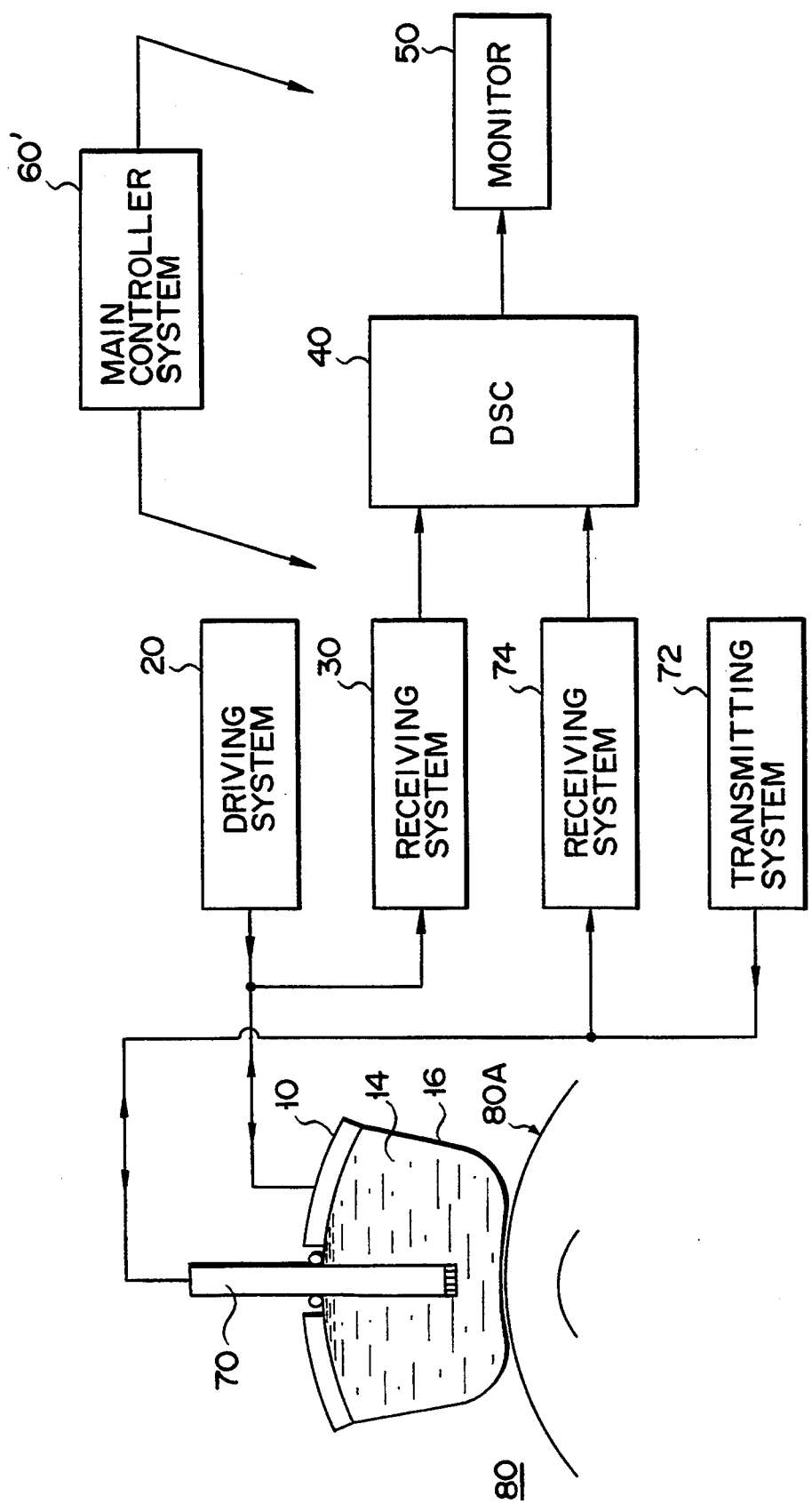
FIG. 5 is a block diagram showing an overall arrangement of an acoustic medical treatment apparatus, such as a stone disintegration apparatus or a hyperthermia apparatus, according to the first embodiment, which is designed to radiate a sound wave on an upper portion of a living body, and specifically showing a system for collectively controlling a section for medical treatment and a section for ultrasonic imaging.

As shown in FIG. 5, a stone disintegration apparatus specified by FIGS. 1 and 5 is designed to radiate a shock wave on an upper portion of a living body and, more specifically, a system for collectively controlling a section for stone disintegration and a section for ultrasonic imaging. An applicator 12 is arranged on a living body 80. The system includes a collective control system 60'.

Figure 6:
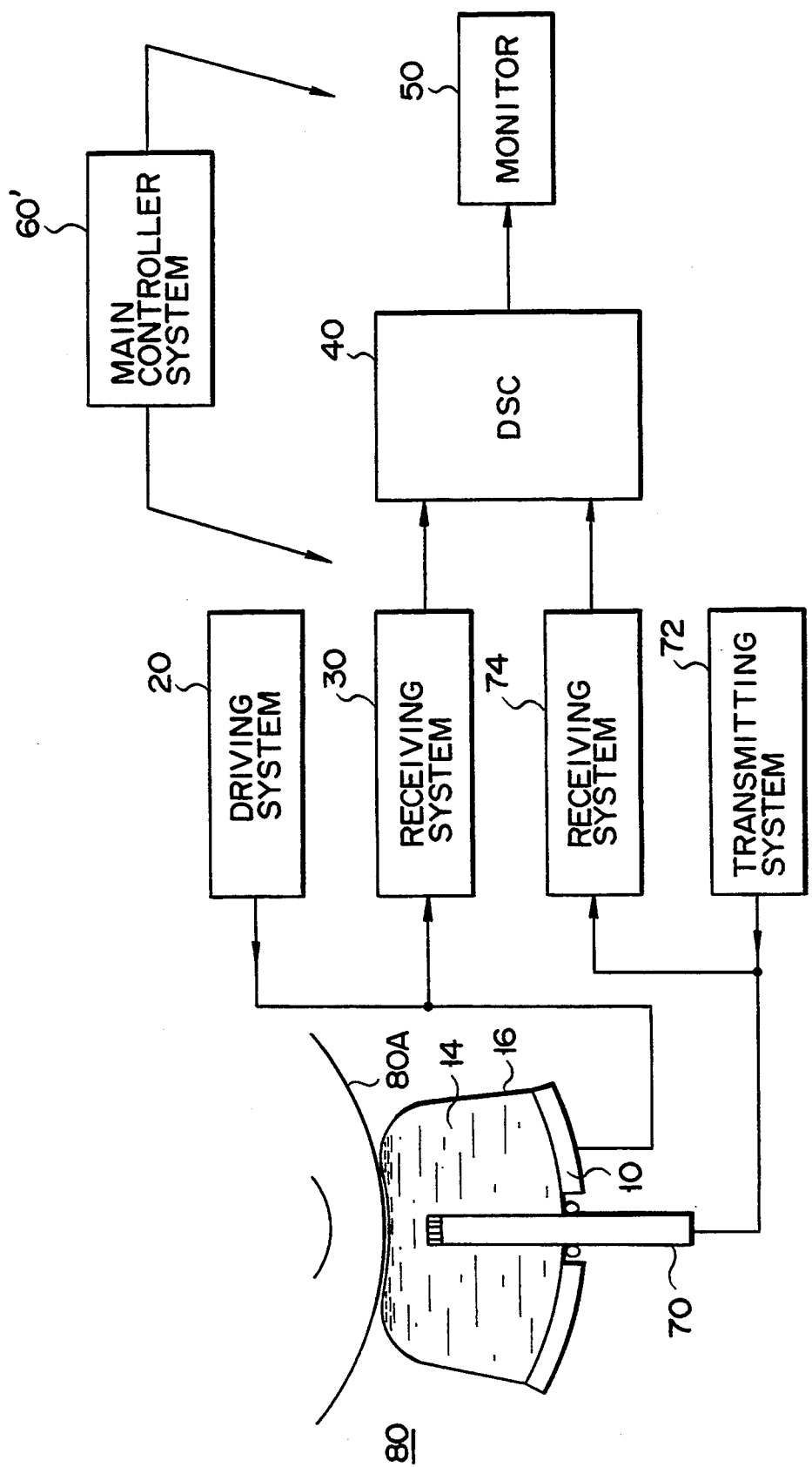
FIG. 6 is a block diagram showing an overall arrangement of an acoustic medical treatment apparatus, such as a stone disintegration apparatus or a hyperthermia apparatus, according to the first embodiment, which is designed to radiate a sound wave on a lower portion of a living body, and specifically showing a system for collectively controlling a section for medical treatment and a section for ultrasonic imaging.

As shown in FIG. 6, a stone disintegration apparatus specified by FIGS. 1 and 6 is designed to radiate a shock wave on a lower portion of a living body and, more specifically, a system for collectively controlling a section for stone disintegration and a section for ultrasonic imaging. An applicator 12 is arranged under a living body. The system includes a main control system 60'.

FIG. 2 is a block diagram showing only components, of a hyperthermia apparatus, associated with a hyperthermia treatment, as an embodiment of the acoustic medical treatment apparatus according to the present invention. In the arrangement shown in FIG. 2, the pulsers 22 constituting the driving system 20 in FIG. 1 are replaced by continuous wave generation drivers 24, thus constituting a section for a hyperthermia treatment. FIGS. 2 and 3 show an overall arrangement of the hyperthermia apparatus. As shown in FIG. 3, this hyperthermia apparatus is designed to radiate a continuous wave or a burst wave on an upper portion of a living body and, more specifically, a system for independently controlling a section for a hyperthermia treatment and a section for ultrasonic imaging. An applicator 12 is arranged on a living body 80. The system includes a concave electroacoustic transducer element controller 60A and an imaging controller 60B.

As shown in FIG. 4, a hyperthermia apparatus specified by FIGS. 2 and 4 is designed to radiate a continuous wave or a burst wave on a lower portion of a living body and, more specifically, a system for independently controlling a section for a hyperthermia treatment and a section for ultrasonic imaging. An applicator 12 is arranged under a living body 80. The system includes a concave electroacoustic transducer element controller 60A and an imaging controller 60B.

As shown in FIG. 5, a hyperthermia apparatus specified by FIGS. 2 and 5 is designed to radiate a continuous wave on an upper portion of a living body and, more specifically, a system for collectively controlling a section for a hyperthermia treatment and a section for ultrasonic imaging. An applicator 12 is arranged on a living body 80. The system includes a main control system 60'.

As shown in FIG. 6, a hyperthermia apparatus specified by FIGS. 2 and 6 is designed to radiate a continuous wave on a lower portion of a living body and, more specifically, a system for collectively controlling a section for a hyperthermia treatment and a section for ultrasonic imaging. An applicator 12 is arranged under a living body 80. The system includes a main control system 60'.

Each of the hyperthermia apparatuses respectively specified by FIGS. 2 and 3, FIGS. 2 and 4, FIGS. 2 and 5, and FIGS. 2 and 6 may use the concave transducer shown in FIGS. 7 or 12. In addition, FIG. 8 shows a positional relationship between a living body and the applicator in each of the hyperthermia apparatuses. Furthermore, the display forms shown in FIGS. 9 to 11 can be used as display forms for displaying the intensities of reception signals in these hyperthermia apparatuses.

According to the present invention, a transducer is divided into a plurality of partial transducers. Weak ultrasonic waves are respectively emitted from these partial transducers, and the reflected waves are respectively detected by the partial transducers to be displayed. Therefore, the state of a propagation path connecting each partial transducer to a focal point can be easily detected, thus eliminating blind regions. With this operation, a shock wave or a continuous wave for medical treatment can be emitted after an optimal propagation path is easily selected and confirmed, thereby providing an acoustic medical treatment apparatus using an electroacoustic transducer element, which can greatly reduce the adverse effects, of unnecessary reflection of waves by a bone, a lung, or an intestinal gas, on a patient, and a pain in a living body, can enhance the safety, and allows efficient medical treatment.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An acoustic medical treatment apparatus comprising:
   sound wave generating means, having a plurality of electroacoustic transducer elements arranged to form a concave surface, said sound wave generating means causing said respective elements to generate sound waves upon application of voltages to said elements, the concave surface focusing the generated sound waves at a selected focal point;
   driving control means for driving/controlling said plurality of electroacoustic transducer elements to selectively generate sound waves for medical treatment and sound waves for non-treatment;
   reception means for receiving sound waves corresponding to a time frame of sound waves reflected from said focal point in correspondence with said plurality of electroacoustic transducer elements when said sound wave generating means is driven by said driving control means to generate sound waves for non-treatment;
   detecting means for detecting obstacles associated with sound wave propagation paths between said plurality of electroacoustic transducer elements and said focal point on the basis of a signal strength of said sound waves corresponding to said time frame received by said reception means, said driving control means including means for stopping selected electroacoustic transducer elements from being driven in correspondence with the obstacles detected by said detecting means in any sound wave propagation path, to selectively generate said sound waves for medical treatment; and
   displaying means for displaying an indication of said obstacles detected by said detecting means and sound wave propagation paths in correspondence with said obstacles.

2. An apparatus according to claim 1, wherein said sound wave generating means is arranged in an applicator having a bag in which an ultrasonic propagation medium is stored, said bag being adapted to be brought into contact with a body surface of a living body.

3. An apparatus according to claim 2, wherein each of said electroacoustic transducer element is a piezoelectric element.

4. An apparatus according to claim 2, wherein each said electroacoustic transducer element includes an electromagnetic induction element.

5. An apparatus according to claim 1, wherein said plurality of electroacoustic transducer elements are arranged in an annular shape.

6. An apparatus according to claim 5, wherein each of said electroacoustic transducer element is a piezoelectric element.

7. An apparatus according to claim 5, wherein each said electroacoustic transducer element includes an electromagnetic induction element.

8. An apparatus according to claim 1, wherein said plurality of electroacoustic transducer elements are arranged as individual circular sound sources.

9. An apparatus according to claim 8, wherein each of said electroacoustic transducer element is a piezoelectric element.

10. An apparatus according to claim 8, wherein each said electroacoustic transducer element includes an electromagnetic induction element.

11. An apparatus according to claim 1, wherein each of said electroacoustic transducer element is a piezoelectric element.

12. An apparatus according to claim 11, wherein said driving control means drives/controls said plurality of electroacoustic transducer elements to selectively generate strong ultrasonic waves as shock waves for a hyperthermia treatment and weak ultrasonic waves for detecting propagation paths of the strong ultrasonic waves.

13. An apparatus according to claim 1, wherein each said electroacoustic transducer element includes an electromagnetic induction element.

14. An apparatus according to claim 1, wherein said driving control means partially drives/controls said plurality of electroacoustic transducer elements of said sound wave generating means when said sound waves for medical treatment are generated by said sound wave generating means.

15. An apparatus according to claim 14, wherein said driving control means include means for turning off a particular electroacoustic transducer element when an obstacle exists in the propagation path of sound waves between said electroacoustic transducer elements and the focal point of said electroacoustic transducer elements.

16. An apparatus according to claim 15, further including means for distinguishing on-driving elements from off-driving elements.

17. An apparatus according to claim 14, wherein said driving control means drives/controls said plurality of electroacoustic transducer elements to selectively generate strong ultrasonic waves as shock waves for disintegrating a stone and weak ultrasonic waves for detecting propagation paths of the strong ultrasonic waves.

18. An apparatus according to claim 1, wherein said driving control means drives/controls said plurality of electroacoustic transducer elements to selectively generate strong ultrasonic waves as shock waves for disintegrating a stone and weak ultrasonic waves for detecting propagation paths of the strong ultrasonic waves.

19. An apparatus according to claim 1, wherein said driving control means drives/controls said plurality of electroacoustic transducer elements to selectively generate strong ultrasonic waves as shock waves for a hyperthermia treatment and weak ultrasonic waves for detecting propagation paths of the strong ultrasonic waves.

20. An apparatus according to claim 1, wherein said detecting means generates information associated with sound wave propagation paths between said plurality of electroacoustic transducer elements and the focal point, as information representing intensities of the reflected waves in correspondence with said plurality of electroacoustic transducer elements with visual effect, on the basis of the reflected wave signals received by said reception means, and displays the generated information.

21. An apparatus according to claim 20, wherein said detecting means displays the generated information associated with the sound propagation paths between said plurality of electroacoustic transducer elements and the focal point in correspondence with an arrangement of said plurality of electroacoustic transducer elements.

22. An apparatus according to claim 20, wherein the display means visually displays the reflected sound waves.

23. An apparatus according to claim 1, wherein said detecting means generates information associated with sound wave propagating paths between said plurality of electroacoustic transducer elements and the focal point, as information representing the reflected waves with a time axis and signal intensities in a graph in correspondence with said plurality of electroacoustic elements, on the basis of the reflected wave signals received by said reception means, and displays the generated information.

24. An apparatus according to claim 23, wherein said generating/display means displays the generated information associated with the sound propagation paths between said plurality of electroacoustic transducer elements and the focal point in correspondence with an arrangement of said plurality of electroacoustic transducer elements.

25. An apparatus according to claim 1, wherein said detecting means generates information associated with sound wave propagation paths between said plurality of electroacoustic transducer means and the focal point, as information having intensity peaks of the reflected waves appended to a pattern indicating the sound wave propagation paths in correspondence with said plurality of electroacoustic transducer elements, on the basis of the reflected wave signals received by said reception means, and displays the generated information.

26. An apparatus according to claim 25, wherein said generating/display means displays the generated information associated with the sound propagation paths between said plurality of electroacoustic transducer elements and the focal point in correspondence with an arrangement of said plurality of electroacoustic transducer elements.

27. An apparatus according to claim 1, wherein said driving control means includes means for differentiating on-driving elements from off-driving elements.

28. An acoustic medical treatment apparatus comprising:
sound wave generating means having a plurality of electroacoustic transducer elements arranged to form a concave surface, for causing said respective elements to generate sound waves upon application of voltages to said elements, said concave surface focusing the generated sound waves at a selected focal point;
driving control means for driving/controlling said plurality of electroacoustic transducer elements to selectively generate sound waves for medical treatment and sound waves for non-treatment;
reception means for receiving sound waves reflected from said focal point in correspondence with said plurality of electroacoustic transducer elements when said sound wave generating means is driven by said driving control means to generate sound waves for non-treatment by examining a time frame corresponding to waves reflected from said focal point;
generating/display means for generating information associated with sound wave propagation paths between said plurality of electroacoustic transducer elements and the focal point on the basis of an intensity of the sound waves reflected from the focal point and received by said reception means and for displaying the generated information, said driving control means including means for selectively prohibiting generation of sound waves for medical treatment by electroacoustic transducer elements corresponding to sound wave propagation paths having an associated reflected sound wave below a specified intensity;

an imaging ultrasonic probe inserted in a substantially central portion of said concave surface of said sound wave generating means along an axial direction toward the focal point, said probe including a large number of small ultrasonic transducers;

tomographic imaging means for scanning/driving each of said ultrasonic transducers of said ultrasonic probe to generate a tomographic image, and means for displaying the tomographic image.

29. An apparatus according to claim 28, wherein the information generated by said generating/display means and the tomographic image obtained by said tomographic imaging means are displayed in correspondence with each other.

30. An apparatus according to claim 29, wherein the information generated by said generating/display means and the tomographic image obtained by said tomographic imaging means are superposed on each other and displayed.

31. An apparatus according to claim 28, wherein driving control means also controls transmission/reception operations of said tomographic image imaging means.

32. An acoustic medical treatment apparatus comprising:

an applicator having a bag in which an ultrasonic medium is stored, said bag being adapted to be brought into contact with a body surface of a living body;

ultrasonic wave generating means, arranged in said applicator and having a plurality of electroacoustic transducer elements forming a concave surface, for generating sound waves upon application of voltages to said elements, the concave surface focusing the sound waves at a focal point;

driving control means for driving/controlling said plurality of electroacoustic transducer elements to selectively generate high-energy ultrasonic waves for medical treatment and low-energy ultrasonic waves for non-treatment;

reception means for receiving ultrasonic waves corresponding to a time frame of sound waves reflected from said focal point in correspondence with said plurality of electroacoustic transducer elements when said ultrasonic wave generating means is driven by said driving control means to generate low-energy ultrasonic waves for non-treatment;

generating/display means for generating information associated with ultrasonic wave propagation paths between said plurality of electroacoustic transducer elements and the focal point on the basis of the ultrasonic waves corresponding to said time frame received by said reception means and for displaying the generated information, said driving control means including means for stopping selected electroacoustic transducer elements from being driven in response to the information associated with the sound wave propagation paths between said selected electroacoustic transducer elements and said focal point, to selectively generate sound waves for medical treatment;

an imaging ultrasonic probe inserted in a substantially central portion of said concave surface of said sound wave generating means along a direction of the focal point, said probe including a large number of small ultrasonic transducers; and tomographic imaging means for scanning/driving each of said ultrasonic transducers of said ultrasonic probe to generate a sector tomographic image, and displaying the sector tomographic image.

33. An acoustic medical treatment apparatus, comprising:

sound wave generating means having a plurality of electroacoustic transducer elements arranged to form a concave surface, the sound wave generating means causing said respective elements to generate sound waves upon application of voltages to said elements, the concave surface of the sound wave generating means focusing the generated sound waves at a selected focal point;

first driving means for driving said plurality of electroacoustic transducer elements to selectively generate sound waves for medical non-treatment;

reception means for receiving sound waves reflected from said selected focal point in correspondence with said plurality of electroacoustic transducer elements when said sound wave generating means is driven by said first driving means to generate sound waves for non-treatment by examining a time frame corresponding to a propagation time of sound wave propagation paths between said electroacoustic transducer elements and said focal point;

detecting means for detecting obstacles associated with the sound wave propagation paths between said plurality of electroacoustic transducer elements and the focal point, on the basis of the signal strength of sound waves reflected from the focal point and received by said reception means; and second driving means including means for driving said electroacoustic transducer elements corresponding to sound wave propagation paths on which no obstacles are detected by said detecting means to selectively generate sound waves for medical treatment and means for stopping said electroacoustic transducer elements from being driven in any sound wave propagation path which corresponds to sound wave propagation paths on which obstacles are detected by said detecting means.

* * * * *